United States Patent
Hellring et al.

(10) Patent No.: US 6,207,871 B1
(45) Date of Patent: *Mar. 27, 2001

(54) HIGH-PURITY META-XYLENE PRODUCTION PROCESS

(75) Inventors: Stuart D. Hellring, Pittsburgh, PA (US); David L. Stern, Mount Laurel, NJ (US)

(73) Assignee: Mobil Oil Corporation, Fairfax, VA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/995,270

(22) Filed: Dec. 19, 1997

(51) Int. Cl.[7] .............................. C07C 15/12; C07C 5/22; C07C 4/12; C07C 5/52
(52) U.S. Cl. .......................... 585/475; 585/488; 585/489; 585/481; 585/474
(58) Field of Search .................... 585/475, 488, 585/489, 481, 474

(56) References Cited

U.S. PATENT DOCUMENTS

| | | | |
|---|---|---|---|
| Re. 30,157 | 11/1979 | Burress | 585/411 |
| Re. 31,919 | 6/1985 | Butter et al. | 502/66 |
| 3,856,872 | 12/1974 | Morrison | 260/668 A |
| 3,856,873 | 12/1974 | Burress | 260/668 A |
| 4,101,595 | 7/1978 | Chen et al. | 260/668 A |
| 4,101,597 | 7/1978 | Breckenridge | 260/668 A |
| 4,224,141 | 9/1980 | Morrison et al. | 208/134 |
| 4,312,790 | 1/1982 | Butter et al. | 252/455 Z |
| 4,899,011 | * 2/1990 | Chu et al. | 585/481 |
| 4,899,012 | * 2/1990 | Sachtler et al. | 585/482 |
| 5,028,573 | * 7/1991 | Brown et al. | 502/66 |
| 5,516,956 | 5/1996 | Abichandani et al. | 585/485 |
| 5,625,104 | 4/1997 | Beck et al. | 585/475 |
| 5,689,027 | * 11/1997 | Abichandani et al. | 585/481 |

FOREIGN PATENT DOCUMENTS

WO 96/16005   5/1996  (WO).

* cited by examiner

*Primary Examiner*—Marian C. Knode
*Assistant Examiner*—Thuan D. Dang

(57) ABSTRACT

There is provided a process for producing high-purity meta-xylene by converting a hydrocarbon feedstream comprising at least about 5 wt % ethylbenzene and at least about 20 wt % meta-xylene, over a single molecular sieve catalyst under ethylbenzene conversion conditions sufficient to provide a primary product stream depleted of more than 50% of the ethylbenzene present in the feedstream. The process can further comprise stripping benzene and/or toluene by-products from the primary product stream to provide a secondary product stream comprising at least about 75 wt % mixed ortho-xylene and meta-xylene; and splitting the secondary product stream by removing substantially all of the ortho-xylene present therein to provide a tertiary product stream comprising at least about 95 wt % meta-xylene.

18 Claims, 2 Drawing Sheets

HIGH-PURITY META-XYLENE PRODUCTION PROCESS

BACKGROUND OF THE INVENTION

1. Field of the Invention

This invention is directed to a process for meta-xylene production using a molecular sieve catalyst system. More specifically, the invention is directed to a process for the catalytic conversion of ethylbenzene with minimized xylene isomerization, and subsequent purification to yield high-purity meta-xylene.

2. Description of the Prior Art

Meta-xylene is a valuable chemical intermediate, with a market price of about 45–60 cents/lb. The principal route for consumption involves oxidation of meta-xylene to isophthalic acid (or ester), the end use of which is for specialty polyester resins for high-performance plastics, such as those used in blow-molded products. For example, the isophthalic acid (ester) can be copolymerized with terephthalic acid (or its ester) and ethylene glycol to produce polyethyleneterephthalate (PET) resins. These resins find use in various products, including plastic bottles, and this market is expected to grow substantially in the coming years.

Meta-xylene may be derived from mixtures of $C_8$ aromatics separated from such raw materials as petroleum naphthas, particularly reformates, usually by selective solvent extraction. The $C_8$ aromatics in such mixtures and their properties are:

|  | Freezing Point (° C.) | Boiling Point (° C.) | Density (Kg/m³) |
|---|---|---|---|
| Ethylbenzene | −95.0 | 136.2 | 869.9 |
| Para-xylene | 13.2 | 138.5 | 863.9 |
| Meta-xylene | −47.4 | 138.8 | 866.3 |
| Ortho-xylene | −25.4 | 144.0 | 883.1 |

Calculated thermodynamic equilibria for the $C_8$ aromatic isomers at 850° F. (454° C.) are:

| Component | Proportion (wt %) |
|---|---|
| Ethylbenzene | 8.5 |
| Para-xylene | 22.5 |
| Meta-xylene | 48.0 |
| Ortho-xylene | 21.5 |
| Total | 100.0 |

Principal sources of the mixtures of $C_8$ aromatics are catalytically reformed naphthas and pyrolysis distillates. The $C_8$ aromatic fractions from these sources vary quite widely in composition but will usually be in the range of 10 wt % to 32 wt % ethylbenzene (EB) with the balance, xylenes, being divided approximately 50 wt % meta-xylene and 25 wt % each of para-xylene and orthxyene.

Individual isomer products may be separated from the naturally occurring mixtures by appropriate physical methods. Ethylbenzene may be separated by fractional distillation, although this is a costly operation. Ortho-xylene may be separated by fractional distillation, and it is so produced commercially. Para-xylene may be separated from the mixed isomers by fractional crystallization, selective adsorption (e.g., the Parex process), or membrane separation.

As is evident in the table of properties above, the boiling point of ethylbenzene is very close to those of para-xylene and meta-xylene. Complete removal of ethylbenzene from the charge by conventional methods, e.g., distillation, is usually impractical. An ethylbenzene separation column may be used in the isomerizer-separator loop or the ethylbenzene may be converted catalytically in the isomerizer-separator loop.

In many processes for xylene isomerization, conversion of ethylbenzene is constrained by the need to hold conversion of xylenes to other compounds to acceptable levels. Thus, although catalytic removal of ethylbenzene is possible, operating conditions are still selected to balance the disadvantages of xylene loss by transalkylation with the conversion of ethylbenzene.

There is currently one commercially practiced method for production of meta-xylene, i.e., the Mitsubishi Gas Chemical Company (MGCC) process. See *Kirk-Othmer Encyclopedia of Chemical Technology*, 3rd ed., Vol. 24, p. 727 (1984), and the publications cited therein, This separations process requires treating a mixture of isomerized xylenes with $HF-BF_3$. Two layers are formed, i.e., a 1:1 molecular complex, meta-xylene-$HBF_3$ layer, and an organic layer containing the remaining xylenes. Meta-xylene is then recovered in 99% purity by thermal decomposition of the meta-xylene-$HBF_3$ complex. Although this method is used commercially by MGCC, the difficulties in dealing with $HF-BF_3$ make this process costly.

UOP has recently announced a sorption-based meta-xylene separations process designated MX-SORBEX but its performance is not presently known.

Thus, the state of the art of meta-xylene production is such that demand for this material continues to increase, while methods for preparing the material lag in commercial practicability. Presently, the processes for producing meta-xylene are limited by cost and purity considerations.

It is, therefore, highly desirable to provide a commercially acceptable process for the production of meta-xylene in substantially pure form. It would also be desirable to provide a process for deriving high-purity meta-xylene from products of other types of reactions to take advantage of readily available resources.

In view of the above considerations, it is clear that existing catalysts and processes for shape selective hydrocarbon conversion are critical to improving the quality and yield of materials suitable for commercial manufacturing. Accordingly, it is one of the purposes of this invention to overcome the above limitations in shape selective hydrocarbon conversion processing, by providing a process for shape selective hydrocarbon conversion processes to produce high-purity meta-xylene.

SUMMARY OF THE INVENTION

It has now been discovered that these and other objectives can be achieved by the present invention, which provides a process for xylene isomerization and ethylbenzene conversion, and optionally p-xylene conversion, over a catalyst.

In one embodiment, the invention is a process for production of purified meta-xylene, comprising:

converting a hydrocarbon feedstream comprising at least about 5 wt % ethylbenzene, at least about 20 wt % meta-xylene, and less than about 5 wt % para-xylene over a molecular sieve catalyst under ethylbenzene conversion conditions sufficient to provide a primary product stream depleted of more than 50%, preferably more than about 95%, of the ethylbenzene present in the feedstream.

The process can further comprise steps of:

stripping benzene and/or toluene by-products from the primary product stream to provide a secondary product stream comprising at least about 75 wt % mixed ortho-xylene and meta-xylene; and splitting the secondary product stream by removing substantially all of the ortho-xylene present therein to provide a tertiary product stream comprising at least about 95 wt % meta-xylene.

Also, the process can further comprise distilling the tertiary product stream to obtain a distillate having further increased meta-xylene content. It is preferred that the distillate produced according to the process comprises at least about 98 wt % meta-xylene.

Moreover, the process can further comprise a preliminary step of:

separating para-xylene from a mixed $C_8$ hydrocarbon feedstream comprising para-xylene, orthoxylene, meta-xylene, and ethylbenzene, to provide the hydrocarbon feedstream.

The process can comprise cofeeding benzene with the hydrocarbon feedstream.

Preferably, the hydrocarbon feedstream comprises from about 1 wt % to about 20 wt % ethylbenzene, from about 20 wt % to about 80 wt % meta-xylene, from about 5 wt % to about 30 wt % ortho-xylene, and from about 0.5 wt % to about 20 wt % para-xylene. More preferably, the hydrocarbon feedstream comprises from about 1 wt % to about 20 wt % ethylbenzene, from about 50 wt % to about 65 wt % meta-xylene, from about 20 wt % to about 30 wt % ortho-xylene, and from about 0 5 wt % to about 5 wt % para-xylene.

The ethylbenzene conversion conditions can comprise a temperature of from about 200° C. to about 550° C., a pressure of from 0 psig to about 1,000 psig, a WHSV of between about 0.1 $hr^{-1}$ and about 200 $hr^{-1}$, and a $H_2$/HC molar ratio of between about 0.2 and about 10. Alternatively, the ethylbenzene conversion conditions can comprise a temperature of from about 325° C. to about 475° C., a pressure of from about 50 psig to about 400 psig, a WHSV of between about 3 $hr^{-1}$ and about 50 $hr^{-1}$, and a $H_2$/HC molar ratio of between about 1 and about 5.

The molecular sieve catalyst useful according to the process of the invention, is preferably a crystalline material. The molecular sieve can, for example, be selected from the group consisting of ZSM-5, ZSM-11, ZSM-12, ZSM-21, ZSM-22, ZSM-23, ZSM-35, ZSM-38, ZSM-48, ZSM-57, ZSM-58 or other molecular sieves such as silicoaluminophosphates, SAPO-5 or SAPO-11. Other suitable materials include, for example, zeolite Beta, zeolite X, zeolite Y, MCM-22, MCM-36, MCM-49, and MCM-56. A preferred molecular sieve is ZSM-5.

The catalyst be modified prior to use in the process, such as by ex situ selectivation, in situ selectivation, coke selectivation, steaming, or a combination thereof. The catalyst can also be modified to include a hydrogenation-dehydrogenation functional metal selected from the group consisting of metals from Groups 3 to 15 of the periodic table. Noble metals, such as platinum and rhenium, are preferred as the hydrogenation-dehydrogenation functional metal.

The process can be performed using a catalyst that has an ortho-xylene $t_{0.3}$ sorption time of greater than about 50 min at 4.5±0.8 mm Hg and 120° C. Also, the process can be performed using a catalyst that produces less than 12 wt % para-xylene when contacting a feed containing 60 wt % meta-xylene, 20 wt % ortho-xylene, and 20 wt % ethylbenzene at a temperature of 426.7° C., a pressure of 150 psig, a WHSV of 20 $hr^{-1}$, and a $H_2$/HC molar ratio of 1.

In another embodiment the invention is a process for production of purified meta-xylene from a mixed $C_8$ aromatic feedstream, comprising:

separating para-xylene from a mixed $C_8$ hydrocarbon fluid comprising para-xylene, orthoxylene, meta-xylene, and ethylbenzene, to provide a hydrocarbon feedstream comprising at least about 5 wt % ethylbenzene, at least about 20 wt % meta-xylene, and less than about 5 wt % para-xylene;

converting the hydrocarbon feedstream over a catalyst comprising a molecular sieve under ethylbenzene conversion conditions sufficient to provide a primary product stream depleted of more than 50% of the ethylbenzene present in the feedstream;

stripping benzene and/or toluene by-products from the primary product stream to provide a secondary product stream comprising at least about 75 wt % mixed ortho-xylene and meta-xylene; and splitting the secondary product stream by removing orthoxylene and heavier materials present therein to provide a tertiary product stream comprising at least about 95 wt % meta-xylene.

Accordingly, the process of the invention is capable of yielding high-purity meta-xylene in a straightforward process that is free of the costly and time-consuming methodology of the prior art. The process can be incorporated into existing processing plants with minimal outlay but with high-purity meta-xylene productivity.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying drawing, wherein.

DETAILED DESCRIPTION OF THE PREFERRED EMBODIMENTS

Figure 1:
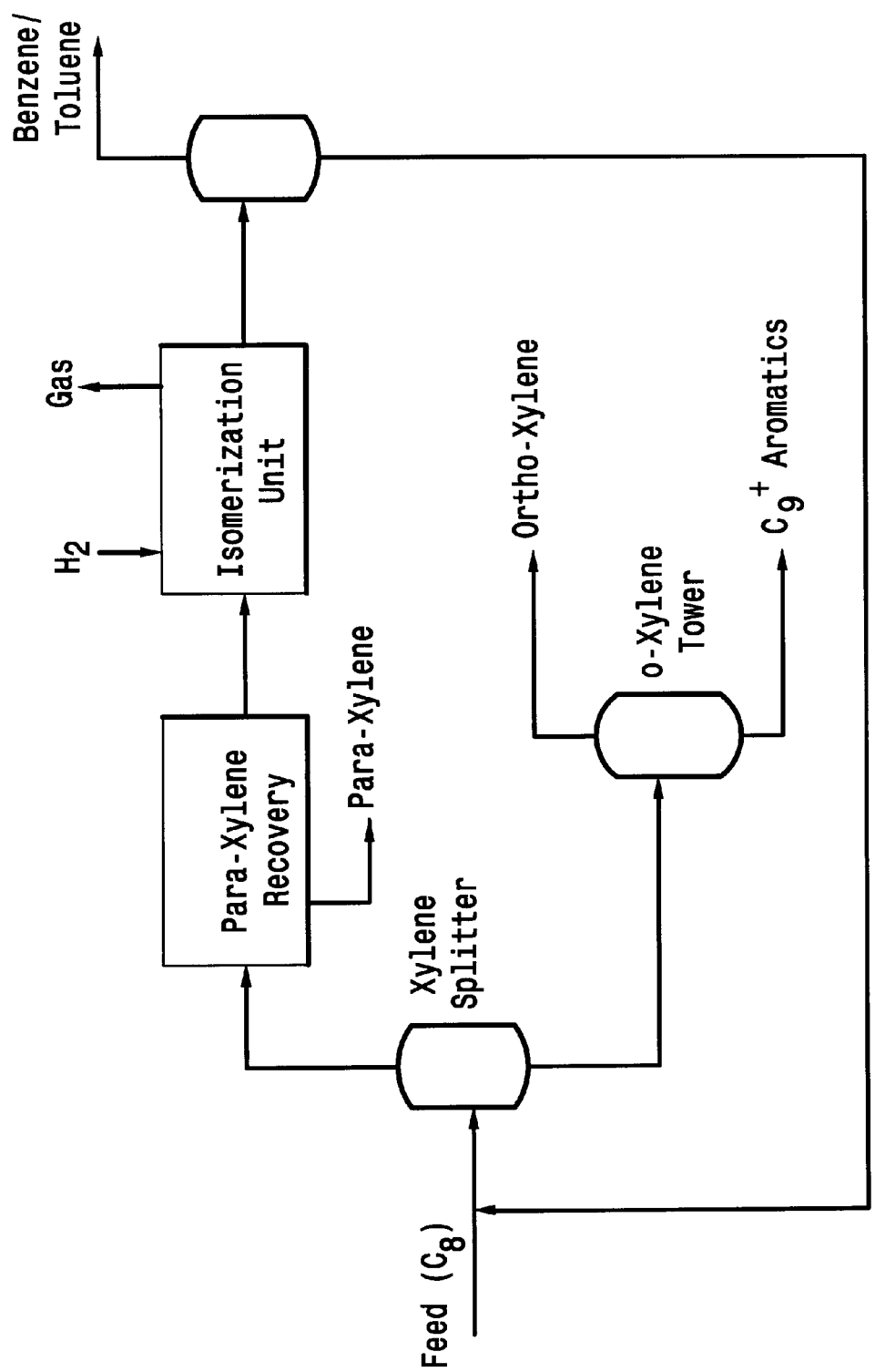
FIG. 1 is schematic illustration of a prior art xylene isomerization processing operation.

The process of the present invention is directed to converting high percentages of the ethylbenzene present in mixed ethylbenzene-xylene-containing feeds, while simultaneously minimizing xylene loss and isomerization.

An embodiment of this invention is a process for aromatics production from a feedstream containing ethylbenzene and at least one xylene, the process comprising contacting the feedstream with a catalyst under ethylbenzene conversion conditions to thereby produce an ethylbenzene-depleted product, the catalyst being effective to produce less than 12 wt % para-xylene when contacting a feed containing 60 wt % meta-xylene, 20 wt % orthoxylene, and 20 wt % ethylbenzene at a temperature of 426.7° C., a pressure of 150 psig (1136 kPaa), a weight hourly space velocity (WHSV) of 20 hr$^{-1}$, and a hydrogen to hydrocarbon (H$_2$/HC) molar ratio of 1. Optionally, benzene can be cofed with the feedstream to promote further depletion of para-xylene from the product. The catalyst may be a silica-bound intermediate pore size molecular sieve that has been modified to adjust activity and/or selectivity, such as by being exposed to one or more of ex situ selectivation, in situ selectivation, coke selectivation, steaming, and the like.

One mode of ethylbenzene (EB) reduction is through disproportionation to benzene (BZ) and diethylbenzene (DEB). A representation of this reaction is:

EB+EB→BZ+DEB     (1)

Another reaction for EB reduction is through dealkylation to BZ and ethylene (ETH). This reaction can be represented as:

EB→BZ+ETH     (2)

The ethylene produced is saturated to ethane using hydrogen in the presence of a hydrogenation catalyst, such as platinum. Another significant reaction is:

EB→XYL     (3)

Several side reactions may also take place. Representations for some of the major side reactions are given below:

| | | | | | | | |
|---|---|---|---|---|---|---|---|
| EB | + | XYL | → | BZ | + | DMEB | (4) |
| EB | + | XYL | → | TOL | + | MEB | (5) |
| XYL | + | XYL | → | TOL | + | TMB | (6) |
| XYL | + | BZ | → | TOL | + | TOL | (7) | wherein: DMEB is dimethylethylbenzene, TOL is toluene, MEB is methylethylbenzene, and TMB is trimethylbenzene.

In the process of this invention, any reaction leading to ethylbenzene destruction or conversion is referred to herein as "ethylbenzene conversion." Moreover, any reaction leading to xylene destruction or conversion is referred to herein as "xylene conversion." Of these reactions, reactions as depicted by equations 1 and 2 are desirable. Further reactions such as 5 and 7 may also be desirable. Also, in addition to the above described reactions, several types of xylene isomerization reactions may occur contemporaneously. Ethylbenzene conversion and xylene loss, as referred to herein, may be determined by comparing the amount of ethylbenzene and total xylenes in the product stream with the amount of those compounds in the feedstream.

This new process comprises contacting a hydrocarbon feed containing C$_8$ aromatics, principally ethylbenzene and xylenes, with a catalyst system under ethylbenzene conversion conditions. Suitable ethylbenzene conversion conditions may include a temperature of from about 200° C. to about 550° C., a pressure of from 0 psig to about 1,000 psig, a WHSV of between about 0.1 hr$^{-1}$ and about 200 hr$^{-1}$, and a hydrogen (H$_2$) to hydrocarbon (HC) molar ratio (H$_2$/HC) of between about 0.2 and about 10.

One embodiment of this invention is a process for isomerizing a feedstream which contains an aromatic C$_8$ mixture of ethylbenzene and xylenes in which the para-xylene concentration is less than that at thermal equilibrium, which process comprises contacting the feed, under ethylbenzene conversion conditions with a catalyst comprising an intermediate pore size molecular sieve, e.g., ZSM-5, which has been modified by being exposed to at least one selectivation sequence, wherein the selectivation sequence includes the steps of contacting the molecular sieve with a selectivating agent and subsequently calcining the selectivated molecular sieve, the intermediate pore size molecular sieve further being combined with a silica binder; whereby at least 50% of the ethylbenzene present in the aromatic C$_8$ mixture is converted to benzene, xylene, or to compounds readily removed by distillation from the aromatic C$_8$ mixture. The conversion of at least 50 wt % of the ethylbenzene present in the feed may be considered to produce an ethylbenzene-depleted product.

The process of the invention is performed over a catalyst comprising a molecular sieve by contacting a meta-xylene-rich hydrocarbon feedstream with the catalyst. As noted, the catalyst is preferably modified in activity and/or selectivity by at least one modification selected from among ex situ selectivation, in situ selectivation, coke selectivation, steaming, adding a hydrogenation/dehydrogenation functional metal, etc., and combinations thereof. These techniques are generally known in the art and are further described hereinbelow.

For example, the modified catalyst can comprise a silica-bound intermediate pore size molecular sieve, e.g., ZSM-5, which has been ex situ selectivated by being coated with at least one coating of an organosilicon selectivating agent, wherein each coating of selectivating agent is applied to the molecular sieve by a process comprising the steps of contacting the catalyst with the organosilicon selectivating agent present in a liquid carrier and subsequently calcining the catalyst in an oxygen-containing atmosphere. The molecular sieve may be combined with the silica binder before or after being coated with the selectivating agent. The molecular sieve may even be combined with the silica binder between subsequent coatings with the selectivating agent. Optionally, the catalyst can be in situ selectivated by being contacted with an organosilicon selectivating agent in a hydrocarbon feedstream under reactor conditions of temperature, pressure, etc. sufficient to deposit a residue of the organosilicon compound on the catalyst. Coke selectivation can be performed by contacting the catalyst with a decomposable organic compound under conditions sufficient to decompose the organic compound while not damaging the catalyst. The catalyst may also be modified by incorporating an inorganic oxide other than silica. Steaming can also be performed to modify the activity of the catalyst as is known in the art. Accordingly, by virtue of selective modification of the catalyst, the isomerization process of the present invention exhibits increased selectivity for ethylbenzene conversion, limited xylene isomerization, and decreased para-xylene production.

The present invention includes both a catalytic process and a separation scheme for producing high-purity meta-xylene which may be incorporated into a xylene isomerization complex. A schematic view of a conventional xylene isomerization processing loop is shown in FIG. 1. Thus, a C$_8$ aromatics stream, such as a heart cut consisting essentially of C$_8$ aromatics, is fed through a xylene splitter apparatus to remove ortho-xylene (and heavier C$_9$$^+$ aromatics) from the mixed xylenes and ethylbenzene. The ortho-xylene and C$_9$$^+$ aromatics are then fed to an ortho-xylene tower where orthoxylene is separated from the heavier components. The product from the xylene splitter is fed to a para-xylene recovery unit, by which a substantial proportion of the para-xylene is removed and recovered. The remaining other C$_8$ materials are then fed to a xylenes isomerization unit with a hydrogen cofeed. The product is distilled to remove benzene and toluene byproducts of the xylene isomerization, and the xylenes (with an increased proportion of para-xylene) is returned as a cofeed to the xylene splitter.

Figure 2:
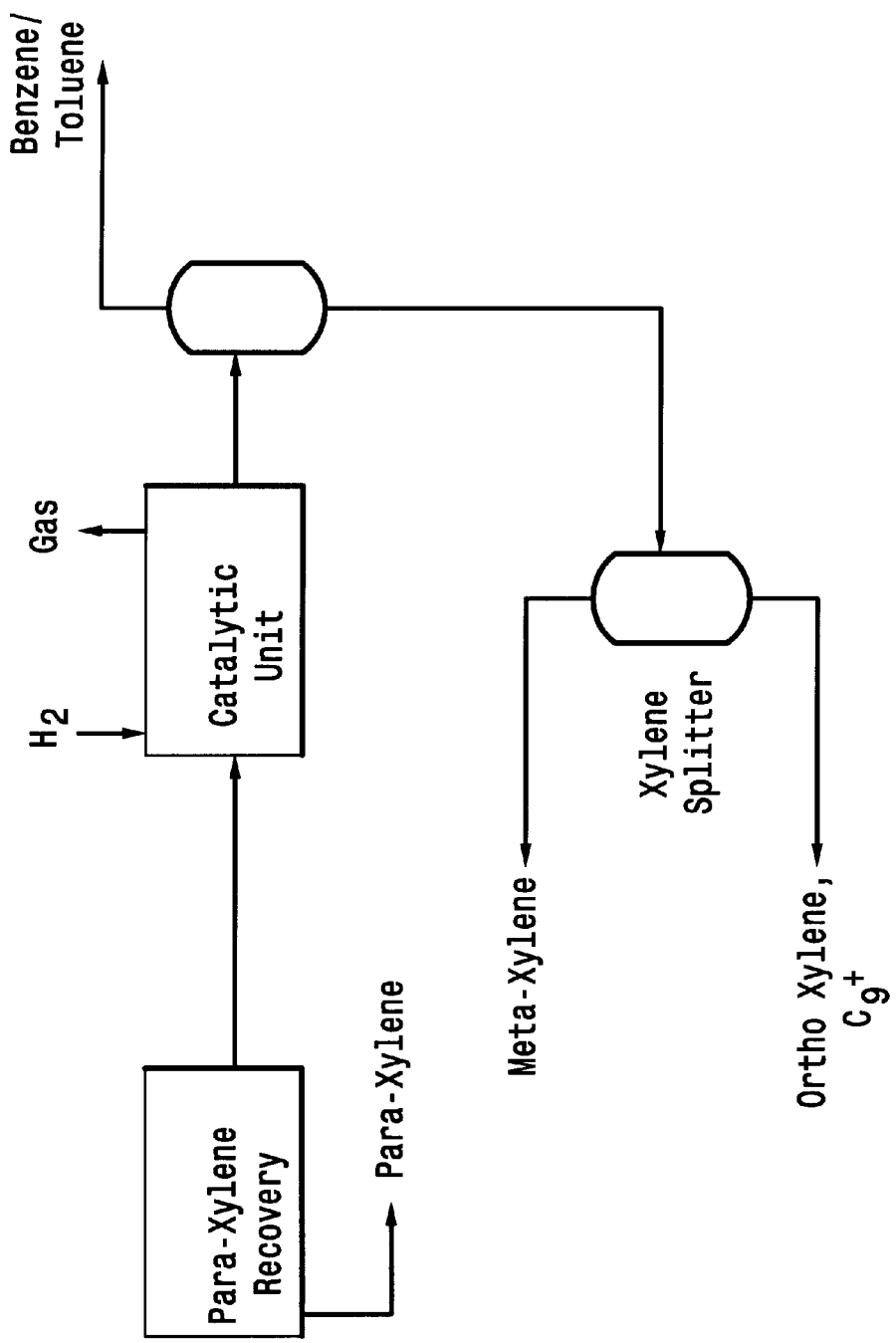
FIG. 2 is a schematic illustration of an exemplary meta-xylene production process operation according to the invention.

The process of the invention, by contrast, permits the development of numerous processing schemes in which meta-xylene yield is important. One exemplary process scheme is illustrated in FIG. 2. Alternatively, the process of the invention may be incorporated into a conventional xylene isomerization plant, such as that illustrated schematically in FIG. 1, in which a portion of the feed to the isomerization unit is passed into a reaction scheme such as that shown in FIG. 2. Thus, the process of the invention involves passing a meta-xylene-rich $C_8^+$ hydrocarbon feed, such as an isomerization unit feed (typically a mixture of about 10 wt % EB, about 1 wt % para-xylene, about 64 wt % meta-xylene, and about 25 wt % ortho-xylene) over a diffusionally restricted catalyst (catalytic unit) to selectively convert both ethylbenzene and para-xylene to very high conversion levels. The resulting ethylbenzene-depleted product is depleted of greater than about 50%, preferably greater than about 95%, and more preferably greater than about 99%, of the ethylbenzene present in the feedstream.

The ethylbenzene-depleted product exiting the catalytic unit is preferably distilled to remove the lighter weight by-products (e.g., light gas, benzene, toluene). Typically, this stripping process will yield a heavier fraction, i.e., a secondary product stream, that is depleted of toluene and/or benzene by products. The secondary product stream will preferably contain at least about 75 wt %, preferably at least about 85 wt %, and more preferably at least about 95 wt %, mixed ortho-xylene and meta-xylene.

Thereafter, the secondary product stream can be fed to a xylene splitter to remove the ortho-xylene and $C_9^+$ aromatics. The light fraction from the ortho-splitter should then consist essentially of very high purity meta-xylene. Typically this tertiary product stream can comprise at least about 85 wt %, preferably at least about 95 wt %, and more preferably at least about 98 wt % meta-xylene.

Preferably, the tertiary product stream is distilled to further increase the purity of the meta-xylene. In a preferred scenario, the process of the invention yields a product comprising at least about 95 wt % meta-xylene, and more preferably at least about 98 wt % meta-xylene. The process can yield a product consisting essentially of meta-xylene.

The process of the invention is capable of using hydrocarbon feeds from many other xylene processing configurations, and is readily adaptable for incorporation into other xylene isomerization processing scenarios. For example, separate reactor schemes for ethylbenzene conversion and isomerization (see, e.g., PCT Publication No. WO 96/16005), liquid-phase isomerization, and the like, may be employed for this purpose. Further it is not necessary that the entire isomerization unit feedstream be diverted to the ethylbenzene conversion unit, but that a small stream be used, whose size is determined based on the amount of meta-xylene desired to be produced. Optionally, benzene may also be cofed to the ethylbenzene conversion unit to increase conversion of para-xylene to toluene, so as to increase the purity of the meta-xylene product thus afforded.

Feedstock

In general, any aromatic $C_8$ mixture containing ethylbenzene and a xylene may be used as feed to the process of this invention. Generally, such a feedstock mixture will typically have an ethylbenzene content in the approximate range of 5 wt % to 60 wt %, an ortho-xylene content in the approximate range of 0 wt % to 35 wt %, a meta-xylene content in the approximate range of 20 wt % to 95 wt % and a para-xylene content in the approximate range of 0 wt % to 25 wt %. For example, the feedstock may contain about 10 wt % to 15 wt % ethylbenzene with the balance xylenes.

Preferably, the hydrocarbon feedstock will contain at least about 30 wt %, more preferably at least about 40 wt %, meta-xylene. Feedstocks meeting this standard are termed "meta-xylene-rich" feedstocks. A preferred feedstock is obtained as the effluent stream from a para-xylene recovery unit. For example, the feedstock may comprise from about 1 wt % to about 20 wt % ethylbenzene, from about 20 wt % to about 80 wt % meta-xylene, from about 5 wt % to about 30 wt % ortho-xylene, and from about 0.5 wt % to about 20 wt % para-xylene. Alternatively, the feedstock can comprise from about 1 wt % to about 20 wt % ethylbenzene, from about 50 wt % to about 65 wt % meta-xylene, from about 20 wt % to about 30 wt % ortho-xylene, and from about 0.5 wt % to about 5 wt % para-xylene.

The $C_8$ feedstream or meta-xylene-rich feedstream contacted with the catalyst may comprise added benzene as a cofeed to facilitate para-xylene conversion to other compounds, such as toluene and trimethylbenzenes. Moreover, in addition to the above, the aromatic $C_8$ mixture may contain non-aromatic hydrocarbons, i.e., naphthenes and paraffins in an amount up to about 30 wt %. In a preferred embodiment, the invention provides means to process a mixture of $C_8$ aromatics such as that derived after other known processing steps such as solvent extraction and distillation from catalytic reforming of a petroleum naphtha to a mixture of reduced ethylbenzene and para-xylene content.

The catalyst of the present invention is especially suitable for the conversion of $C_8$ aromatic streams that contain from about 1 wt % to about 60 wt % ethylbenzene, e.g., from about 1 wt % to about 50 wt % ethylbenzene. This range spans the range of ethylbenzene concentrations of streams that are derived from a reformer and a pyrolysis gasoline unit. The present process may exhibit cracking of normal and branched paraffins of the type present in unextracted $C_8$ aromatic streams.

Process Conditions

In accordance with the present invention, the above described feedstock may be contacted with the catalyst system under suitable conversion conditions to effect ethylbenzene conversion and optionally para-xylene conversion. Conditions effective to accomplish ethylbenzene conversion are termed "ethylbenzene conversion conditions." Examples of these conversion conditions include a temperature of from about 200° C. to about 550° C., a pressure of from 0 psig to about 1,000 psig, a WHSV of between about 0.1 $hr^{-1}$ and about 200 $hr^{-1}$, and an $H_2$/HC molar ratio of between about 0.2 and about 10. An alternative to these conversion conditions may include a temperature of from about 325° C. to about 475° C., a pressure of from about 50 psig to about 400 psig, a WHSV of between about 3 $hr^{-1}$ and about 50 $hr^{-1}$, and a $H_2$/HC molar ratio of between about 1 and about 5. The WHSV is based on the weight of catalyst composition, i.e., the total weight of active catalyst and, if used, binder therefor.

One function of the catalyst system is to effect ethylbenzene conversion with minimal isomerization of xylenes. The ethylbenzene conversion products tend to be compounds that are more easily recovered or are more easily separated from the nixed xylenes. Optimally, the component effective for ethylbenzene conversion may be distinguished by limited capability for xylene isomerization. This limited capability for xylene isomerization by the catalyst appears to be associated with a diffusion resistance for xylenes, particularly ortho-xylene and meta-xylene, as well as low isomerization activity of xylenes.

To effect high levels of conversion of ethylbenzene, while without excessive loss of xylenes to heavier aromatics and other components, the feedstream should be contacted with the catalyst under the ethylbenzene conversion conditions described above. The conversion process described herein may be carried out as a batch type, semi-continuous, or continuous operation. After use in a moving or fluidized bed reactor, the catalyst can be regenerated, in a regeneration zone in which the coke is burned from the catalyst in an oxygen-containing atmosphere, e.g., air, at an elevated temperature after which the regenerated catalyst is recycled to the conversion zone for further contact with charge stock. In a fixed bed reactor, regeneration can be carried out in a conventional manner by using initially an inert gas containing a small amount of oxygen (0.5 to 2 volume percent) to burn coke in a controlled manner so as to limit the temperature to a maximum of about 450° C. to 500° C.

After the conversion process, the meta-xylene can be recovered by distillation.

One result of the process of this invention is the conversion of 15% to 100% of the ethylbenzene contained in the mixed xylene feed to benzene and other components that are relatively easily removed from the mixed xylene stream. For example, ethylbenzene conversion levels of greater than 50% are easily accomplished, e.g., greater than 70%, e.g., greater than 80%, e.g., greater than 85%, e.g., 90% or more by weight. The high conversion of ethylbenzene using the selective catalyst and conversion conditions of the present invention results in a molar ratio of benzene produced to ethylbenzene consumed of greater than 0.5, e.g., greater than 0.65, e.g., greater than 0.75, e.g., greater than 0.80.

Catalyst System

The alpha value of the catalyst which is effective to convert ethylbenzene with minimized xylene isomerization may be at least 5. The alpha value of that component may range from 75 to 5000 or more, and it may even range from 100 to 2000. The alpha value is an approximate indication of the catalytic cracking activity of the catalyst compared to a standard catalyst and it gives the relative rate constant (rate of normal hexane conversion per volume of catalyst per unit time.) It is based on the activity of an amorphous silica-alumina cracking catalyst taken as an alpha of 1 (Rate Constant=0.016 $sec^{-1}$). The Alpha Test is described in U.S. Pat. No. 3,354,078 and in *J. Catalysis* 4:522–529 (August 1965): *J. Catalysis* 6:278 (1966); and *J. Catalysis* 61:395 (1980), each incorporated herein by reference as to that description. It is noted that intrinsic rate constants for many acid-catalyzed reactions are proportional to the alpha value for a particular crystalline silicate catalyst (see "The active site of acidic aluminosilicate catalysts," *Nature*, 309(5959):589–591, (14 Jun. 1984)). The alpha value of the catalyst may be increased by treating the catalyst with nitric acid or by mild steaming as discussed in U.S. Pat. No. 4,326,994.

The xylene diffusion properties of this component may be such that, under ethylbenzene conversion conditions, the catalyst is capable of only a limited amount of xylene somerization. For example, the ethylbenzene conversion catalyst may be one that meets the following test: producing less than 12 wt % para-xylene when contacting a feed containing 60 wt % meta-xylene, 20 wt % ortho-xylene, and 20 wt % ethylbenzene at a temperature of 426.7° C., a pressure of 150 psig (1136 kpaa), a weight hourly space velocity (WHSV) of 20 $hr^{-1}$, and a hydrogen to hydrocarbon molar ratio of 1. In the above test, the ethylbenzene conversion catalyst may even produce smaller amounts of para-xylene, e.g., less than 10 wt % para-xylene, e.g., less than 6 wt % para-xylene, e.g., less than 3 wt %, e.g., less than 1 wt % para-xylene, while converting more than 15 wt %, e.g., more than 30 wt % or even more than 65 wt % of the ethylbenzene. See U.S. Pat. No. 5,689,027, incorporated herein by reference.

As pointed out above, the parent molecular sieve component of this catalyst may be one characterized by a Constraint Index within the approximate range of 1 to 12. This parameter embraces a number of molecular sieves as otherwise described herein. When, as in an embodiment described below, the molecular sieve of this component is ZSM-5, the requisite diffusional properties may be provided by providing ZSM-5 in suitable crystal sizes as will be further described herein, which, optionally, have been further coated, as will be more fully described below, at least once with a silicon selectivating agent described herein, wherein each coating of selectivating agent is applied to the molecular sieve by a process comprising the steps of contacting the molecular sieve with a liquid organosilicon selectivating agent present in a liquid carrier and subsequently calcining the catalyst in an oxygen-containing atmosphere. As mentioned above, the molecular sieve may be bound with silica before being coated, after being coated or between successive coatings. Suitable selectivating agents are those which inhibit the diffusivity of the molecular sieve, particularly, the diffusivity of the molecular sieve to ortho-xylene and meta-xylene. Alternatively, the desired diffusional properties may be also achieved through the use of trim-selectivation or coke selectivation, as further described herein, either alone or in combination with one or more coatings of the selectivating agent described above.

Catalysts useful in this invention comprise a catalytic molecular sieve, such as zeolite. The molecular sieve is preferably an intermediate pore size zeolite. Examples of intermediate pore size zeolites useful in this invention include ZSM-5 (U.S. Pat. No. 3,702,886 and Re. 29,948); ZSM-1 (U.S. Pat. No. 3,709,979); ZSM-12 (U.S. Pat. No. 3,832,449); ZSM-21 (U.S. Pat. No. 4,046,859); ZSM-22 (U.S. Pat. No. 4,556,447); ZSM-23 (U.S. Pat. No. 4,076,842); ZSM-35 (U.S. Pat. No. 4,016,245); ZSM-38 (U.S. Pat. No. 4,406,859); ZSM48 (U.S. Pat. No. 4,397,827); ZSM-57 (U.S. Pat. No. 4,046,685); and ZSM-58 (U.S. Pat. No. 4,417,780).

Other useful catalytic molecular sieves include MCM-22, MCM-36, MCM49, MCM-56, silicoaluminophosphates such as SAPO-5, SAPO-11, and other zeolites including zeolite X, zeolite Y, and zeolite Beta, and the like. In any event, while much of the discussion herein may be directed to ZSM-5 zeolites, the artisan will recognize that similar considerations apply to other molecular sieves.

The molecular sieve has a Constraint Index within the approximate range of 1 to 12. The method by which Constraint Index is determined is described in U.S. Pat. No. 4,016,218, incorporated herein by reference. Alternatively, the molecular sieve can be characterized according to pore size. Thus, the molecular sieve useful according to the invention has a pore size of less than about 7 Å, preferably from about 5 Å to less than about 7Å.

The molecular sieve also has a silica to alumina ($SiO_2/Al_2O_3$) molar ratio of at least about 5, preferably from about 12 to about 100, and more preferably from about 20 to about 80. The silica to alumina ratio referred to may be determined by conventional analysis, such as elemental analysis or nuclear magnetic resonance spectroscopy. This ratio is meant to represent, as closely as possible, the molar ratio in the rigid anionic framework of the molecular sieve crystal and to exclude silicon and aluminum in the binder or in cationic or other form within the channels.

The catalyst may be characterized according to its xylene diffusion or xylene sorption properties. In particular, it has been found that the catalyst should possess an equilibrium sorption capacity of xylene, which can be either para-, meta-, ortho-, or a mixture thereof, frequently para-xylene, since this isomer reaches equilibrium within the shortest time, of at least 1 g per 100 g of molecular sieve measured at 120° C. and a xylene pressure of 4.5±0.8 mm of mercury (493 Paa to 707 Paa). The catalyst should also have an ortho-xylene sorption time ($t_{0.3}$), i.e., the time required to achieve 30% of the xylene sorption capacity, of greater than 50 minutes (at the same conditions of temperature and pressure). A catalyst having such properties can be used to achieve the desired level of ethylbenzene conversion while maintaining the desired level of xylene loss. The sorption measurements may be carried out gravimetrically in a thermal balance. The sorption test is described in U.S. Pat. Nos. 4,117,026; 4,159,282; 5,173,461; and Re. 31,782, each incorporated herein by reference.

The xylene diffusion properties of the catalyst may be such that, under hydrocarbon conversion conditions, the catalyst is capable of only a limited amount of xylene isomerization. For example, the catalyst may be one that meets the following test: producing less than 12 wt % para-xylene when contacting a feed containing 60 wt % meta-xylene, 20 wt % ortho-xylene, and 20 wt % ethylbenzene at a temperature of 426.7° C., a pressure of 150 psig (1136 kpaa), a weight hourly space velocity (WHSV) of 20 $hr^{-1}$, and a hydrogen to hydrocarbon ($H_2$/HC) molar ratio of 1. In the above test, the catalyst modified according to the invention may even produce smaller amounts of p-xylene, preferably, less than 10 wt % p-xylene, more preferably less than 3 wt %, and still more preferably, less than 1 wt % p-xylene, while converting more than 15 wt %, preferably more than 30 wt %, or more preferably more than 65 wt % of the ethylbenzene.

The suitable molecular sieve may be employed in combination with a support or binder material such as, for example, a porous inorganic oxide support or a clay binder. For example, it may be desirable to formulate the catalyst of the invention with another material resistant to the temperature and other conditions of the hydrocarbon conversion process. Illustrative examples of binder materials include synthetic or naturally occurring substances as well as inorganic materials such as clay, silica, and/or metal oxides, such as alumina, vanadia, beryllia, thoria, magnesia, titania, zirconia, boria, and combinations thereof. The preferred binder is primarily silica. The metal oxides may be naturally occurring or in the form of gelatinous precipitates or gels including mixtures of silica and metal oxides.

Naturally occurring clays that can be composited with the molecular sieve include those of the montmorillonite and kaolin families, which families include the subbentonites and the kaolins commonly known as Dixie, McNamee, Georgia, and Florida clays, or others in which the main mineral constituent is halloysite, kaolinite, dickite, nacrite, or anauxite. Suitable clay materials include, by way of example, bentonite and kieselguhr. Such clays can be used in the raw state as originally mined or initially subjected to calcination, acid treatment, or chemical modification.

The relative proportion of suitable crystalline molecular sieve to the total composition of catalyst and binder or support may be from about 1 wt % to about 99 wt %, preferably from about 30 wt % to about 90 wt %, and more preferably from about 50 wt % to about 80 wt %, of the composition.

The form and the particle size of the catalyst are not critical to the present invention and may vary depending, for example, on the type of reaction system employed. Non-limiting examples of the shapes of the catalyst in the present invention include balls, pebbles, spheres, extrudates, channeled monoliths, honeycombed monoliths, microspheres, pellets, or structural shapes, such as lobes, trilobes, quadralobes, pills, cakes, honeycombs, powders, granules, and the like, formed using conventional methods, such as extrusion or spray drying.

Exemplary procedures for preparing silica bound molecular sieves are described in U.S. Pat. Nos. 4,582,815; 5,053,374; and 5,182,242. For example, a procedure for binding a molecular sieve involves an extrusion process. Thus, a silica-bound molecular sieve may be prepared by a process comprising the steps of. (a) mulling and then extruding a mixture comprising water, a molecular sieve, colloidal silica and sodium ions under conditions sufficient to form an extrudate having an intermediate green strength sufficient to resist attrition during ion exchange step (b) set forth hereinafter;

(b) contacting the extrudate of step (a) with an aqueous solution comprising ammonium cations under conditions sufficient to exchange cations in the molecular sieve with ammonium cations; and (c) calcining the ammonium exchanged extrudate of step (b) under conditions sufficient to generate a hydrogen form of the molecular sieve and increase the crush strength of the extrudate.

Another method of silica binding uses a suitable silicone resin, e.g., a high molecular weight, hydroxy functional silicone resin, in a method disclosed in U.S. Pat. Nos. 4,631,267 and 3,090,691. Extrusion aids, such as methyl cellulose materials may also be useful in the preparation of the catalysts of this invention.

The molecular sieve, either directly or via initial ammonium exchange followed by calcination, may be hydrogen exchanged such that a predominant proportion of its exchangeable cations are hydrogen ions. It is contemplated that more than 50% and preferably more than 75% of the cationic sites of the crystalline molecular sieve will be occupied by hydrogen ions.

Original ions, e.g., alkali or alkaline earth metal, of the as-synthesized molecular sieve can be replaced in accordance with techniques well known in the art, at least in part, by ion exchange with other ions. Typical ion exchange techniques would be to contact the synthetic molecular sieve with a solution containing a salt of the desired replacing ion or ions. Examples of such salts include the halides, e.g., chlorides, nitrates, and sulfates. Representative ion exchange techniques are disclosed in a wide variety of patents including U.S. Pat. Nos. 3,140,251 and 3,140,253, each incorporated herein by reference.

Hydrogenation-Dehydrogenation Functional Modification

A hydrogenation-dehydrogenation functional metal can be incorporated into the catalyst of the invention. Such metals are known in the art to reduce ethylbenzene by-product in hydrocarbon conversion processes. See, e.g., U.S. Pat. No. 5,498,814, incorporated herein by reference.

Any metal possessing the desired hydrogenation-dehydrogenation function can be used in the modification method of the invention. These are termed "functional metals." Examples of such functional metals include the oxide, hydroxide, sulfide, or free metal (i.e., zero valent) forms of metals in the Groups 3 to 15 of the periodic table. Preferred metals include Group 8, 9, and 10 metals (i.e., Pt, Pd, Ir, Rh, Os, Ru, Ni, Co, and Fe), Group 7 metals (i.e., Mn, Tc, and Re), Group 6 metals (i.e., Cr, Mo, and W), Group 15 metals (i.e., Sb and Bi), Group 14 metals (i.e., Sn and Pb), Group 13 metals (i.e., Ga and In), Group 11 metals (i.e., Cu, Ag, and Au), and Group 12 metals (i.e., Zn, Cd, and Hg). Noble metals (i.e., Pt, Pd, Ir, Rh, Os, Re, Ru, Mo, and W) are preferred.

Combinations or mixtures of catalytic forms of such noble or non-noble metal, such as combinations of Pt with Sn, may be used. The valence state of the metal is preferably reduced, e.g., when this component is in the form of an oxide or hydroxide. The reduced valence state of the functional metal may be attained, in situ, during the course of a reaction, when a reducing agent, such as hydrogen, is included in the feed to the reaction.

The functional metal may be incorporated into the catalyst by methods known in the art, such as ion exchange, impregnation, or physical admixture. For example, solutions of appropriate metal salts may be contacted with the remaining catalyst components, either before or after selectivation of the catalyst, under conditions sufficient to combine the respective components. The metal-containing salt is preferably water-soluble. Examples of such salts include chloroplatinic acid, tetraamine platinum complexes, platinum chloride, tin sulfate, and tin chloride. The metal may be incorporated in the form of a cationic, anionic, or neutral complex such as $Pt(NH_3)_4^{2+}$, and cationic complexes of this type will be found convenient for exchanging metals into the molecular sieve. Anionic complexes such as the vanadate or metatungstate ions are also useful for impregnating metals into the molecular sieves. Incorporation is preferably undertaken in accordance with the method described in U.S. Pat. No. 4,312,790. After incorporation of the metal, the catalyst can then be filtered, washed with water, and calcined at temperatures of from 250° C. to 500° C.

Addition of the metal can be accomplished through mixing the catalyst with a solution, preferably aqueous, of an appropriate metal salt, acid oxide, or other metal complex. The mixing can be performed at about ambient temperature or at elevated temperatures, e.g., through reflux. In the case of an acidic form of a catalyst, it may be desirable to perform a first exchange to provide an ammonium form, followed by a second exchange to provide the metal form.

The amount of functional metal may be that amount which increases the catalytic ability of the overall catalyst to catalytically hydrogenate or dehydrogenate an organic compound, e.g., ethylene, under sufficient hydrogenation or dehydrogenation conditions. This amount is referred to herein as a catalytic amount. The amount of the functional metal is suitably from about 0.001 wt % to 10 wt %, preferably from about 0.05 wt % to about 5 wt %, more preferably from about 0.1 wt % to about 2 wt %, based on the total weight of the modified catalyst However the artisan will recognize that the required amount of the functional metal will vary with the nature of the component, with less of the highly active noble metals being required than of the less active base metals.

Selectivation of Catalysts

Various methods are known in the art for increasing the selectivity of molecular sieve catalysts. One such method is to modify the catalyst by treatment with a "selectivating agent." For example, U.S. Pat. Nos. 5,173,461; 4,950,835; 4,927,979; 4,465,886; 4,477,583; 4,379,761; 4,145,315; 4,127,616; 4,100,215; 4,090,981; 4,060,568; and 3,698,157 disclose specific methods for contacting a catalyst with a selectivating agent containing silicon ("organosilicon compound"). U.S. Pat. Nos. 5,367,099; 5,382,737; 5,365,004; 5,403,800; and 5,406,015, and PCT Publication No. WO94/27934, also disclose methods for silicon-based selectivation of catalysts.

In accordance with one selectivation method, called "ex situ selectivation" or "preselectivation," catalyst is modified by being exposed to one or more treatments with a silicon compound in a liquid carrier, each treatment being followed by calcination of the treated material in an oxygen-containing atmosphere, e.g., air. Thus, the molecular sieve, e.g., HZSM-5, is treated at least once, preferably at least twice, with a fluid medium comprising a silicon compound and a carrier fluid. The carried fluid is then removed, e.g., evaporated, leaving a deposited residue of the silicon compound on the catalyst. Subsequently, the coated catalyst is calcined to convert the silicon-containing material to a silica material containing little or no residual carbon. More particularly, for example, with reference to the above-mentioned steps (a)–(c), this first selectivation method may involve the additional steps of:

(d) contacting the calcined extrudate of step (c) with a liquid comprising a liquid carrier and at least one organosilicon selectivating agent having at least two silicon atoms per molecule under conditions sufficient to incorporate the organosilicon selectivating agent in the extrudate, (e) calcining the extrudate of step (d) under conditions sufficient to decompose the organosilicon selectivating agent and to remove any residue of the liquid carrier from the extrudate; and, optionally, (f) repeating selectivation steps (d) and (e) at least once. These modified catalysts have been observed to have improved properties in certain hydrocarbon conversion processes.

Another method for selectivating a catalyst, known as "trim selectivation" or "in situ selectivation, involves passing a feed stream comprising hydrogen and an aromatic (e.g., toluene) or a paraffin (e.g., hexane or decane) and an organosilicon compound over the molecular sieve under "in situ selectivation conditions," i.e., conditions sufficient to deposit a residue of the organosilicon compound on the molecular sieve. Suitable organosilicon compounds include volatile organosilicon compounds having sufficient vapor pressure for proper deposition under in situ selectivation conditions. Toluene may comprise 50 wt % to 100 wt %, e.g., at least 80 wt %, of the hydrocarbons in the feedstock. Other hydrocarbons, such as benzene, xylenes, and trimethylbenzenes, may also be present in the feedstock for in situ selectivation.

In situ selectivation protocols typically comprise conditions include temperatures ranging from about 100° C. to about 600° C., preferably from about 300° C. to about 500° C.; pressures ranging from about 0 to about 2000 psig, preferably from about 15 psig to about 800 psig; a $H_2/HC$ mole ratio of from about 0 (i.e., no hydrogen is present) to about 20, preferably from about 1 to about 4; at a WHSV of from about 0.1 $hr^{-1}$ to about 100 $hr^{-1}$, preferably from about 0.1 $hr^{-1}$ to about 10 $hr^{-1}$. Upon thermolysis, a siliceous coating is deposited on the molecular sieve surface, eliminating surface activity and enhancing shape-selectivity.

The presence of a sufficient amount of hydrogen in the in situ-selectivation feedstock is necessary to prevent rapid aging of the catalyst during the selectivation process resulting in an excessive reduction in the catalyst activity, possibly accompanied by a reduction in selectivity for ethylbenzene conversion. This rapid aging is believed to result from a rapid build-up of excessive amounts of carbonaceous deposits (i.e., coke), which may even extend into the pore system of the molecular sieve in the catalyst. However, even when hydrogen is used in optimal fashion to prevent aging during the selectivation process, a small amount of carbonaceous deposit forms on the catalyst. As a result of this carbonaceous deposit, the elemental analysis of the in situ-selectivated catalyst reveals a carbon content significantly greater than the carbon content of the fresh catalyst prepared by the multiple impregnation method described herein. More particularly, the in situ-selectivated catalyst may contain at least 2 wt %, e.g., at least 4 wt %, of carbon by elemental analysis, whereas the catalyst prepared by the multiple impregnation method may contain less than 0.5 wt % of carbon as measured by elemental analysis. These weight percentages are expressed in terms of the weight of the entire catalyst including the molecular sieve, binder, and optional components, e.g., hydrogenation-dehydrogenation components.

The present catalyst may be subjected to controlled coking or coke selectivation. This optional coke selectivation may involve contacting the catalyst with a thermally decomposable organic compound at an elevated temperature in excess of the decomposition temperature of the compound but below the temperature at which the crystallinity of the catalyst is adversely affected.

While not wishing to be bound by theory, it is believed that the advantages of the present invention are obtained by rendering acid sites on the external surfaces of the catalyst substantially inaccessible to reactants while increasing catalyst tortuosity. Acid sites existing on the external surface of the catalyst are believed to isomerize the xylenes to equilibrium. By reducing the availability of these acid sites, incoming xylene distribution can be maintained.

The organosilicon compound used to selectivate the molecular sieve may be a silicone, siloxane, or silane. Silicones are defined herein as those compounds wherein silicon atoms are bonded to one another via oxygen atoms. Silanes are defined herein as those compounds wherein silicon atoms are bonded directly to one another. These organosilicon compounds may have at least 2 silicon atoms per molecule. The molecular weight of the silicon compound employed as a selectivating agent may be between 80 and 20,000, and is preferably within the approximate range of 150 to 10,000.

The kinetic diameter of the selectivating agent is preferably larger than the molecular sieve pore diameter, to avoid entry of the selectivating agent into the molecular sieve pores and any concomitant reduction in the internal activity of the molecular sieve. When a silicon compound is used that is of a size small enough to enter the pores of the catalyst crystal, it may be desirable to use the sodium form of the molecular sieve rather than the hydrogen form.

The silicon compound used to selectivate the present molecular sieve may be constructed of a siloxy backbone structure capped with terminal groups. This siloxy backbone structure may be a chain structure represented by the formula:

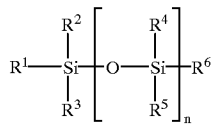

wherein $R^1$, $R^2$, $R^3$, $R^4$, $R^5$, and $R^6$ are independently selected from hydrogen, fluorine, hydroxy, alkyl, aralyl, alkaryl, alkoxy, or fluoro-alkyl. The hydrocarbon substituents generally contain from 1 to 10 carbon atoms and preferably are methyl, ethyl, or phenyl groups. The variable n is an integer of at least 2, and generally in the range of from 2 to about 1000.

Preferred examples of silicone compounds having a chain siloxy backbone structure given above are those wherein $R^1$ and $R^6$ are independently hydrogen, methyl, or phenyl; $R^2$, $R^3$, $R^4$ and $R^5$ are independently methyl or phenyl; and m is from 1 to 100, e.g., from 1 to 25, e.g., from 1 to 10, e.g., from 1 to 4. Preferably, no more than one phenyl group is bonded to each silicon atom. Particular examples of such silicone compounds having a chain siloxy backbone structure include hexamethyldisiloxane, decamethyltetrasiloxane, and diphenyltetramethyldisiloxane.

Representative silicone compounds include dimethylsilicone, diethylsilicone, phenylmethylsilicone, methylhydrogensilicone, ethylhydrogensilicone, phenylhydrogensilicone, methylethylsilicone, phenylethylsilicone, diphenylsilicone, methyltrifluoropropylsilicone, ethyltrifluoropropylsilicone, polydimethylsilicone, tetrachlorophenylmethylsilicone, tetrachlorophenylethylsilicone, tetrachlorophenylhydrogensilicone, tetrachlorophenylphenylsilicone, methylvinylsilicone, and ethylvinylsilicone.

This siloxy backbone structure may also be a cyclic structure represented by the formula:

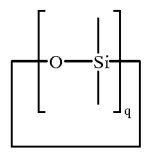

where q is from 2 to 10. Branched chain structures and composite chain/cyclic structures are also possible for the siloxy backbone of the silicone selectivating agent.

The silicone compound need not be linear, but may be cyclic, for example, hexamethylcyclotrisiloxane, octamethylcyclotetrasiloxane, hexaphenylcyclotrisiloxane, octaphenylcyclotetrasiloxane, and decamethylcyclopentasiloxane. Particular examples of silicone compounds having a branched siloxy backbone structure are tris-(trimethylsiloxy)-phenylsilane and tris-(trimethylsiloxy)-silane.

Useful silanes, disilanes, or alkoxysilanes include organic-substituted silanes having the general formula:

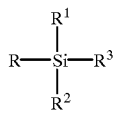

wherein R is a reactive group such as hydrogen, alkoxy, halogen, carboxy, amino, acetamide, or trialkylsilyl. $R^1$, $R^2$, and $R^3$ can be the same as R or an organic radical which may include $C_1$–$C_{40}$ alkyl; alkyl or aryl carboxylic acid wherein the organic portion of the alkyl is a $C_1$–$C_{30}$ alkyl and the aryl group is a $C_6$–$C_{24}$ aryl; $C_6$—$C_{24}$ aryl groups which may be further substituted; alkylaryl; and $C_7$–$C_{30}$ arylalkyl groups. Preferably, the alkyl group of an alkyl silane is between 1 and 4 carbon atoms in chain length. Mixtures may also be used.

The silane compounds useful as selectivating agents according to the present method may have structures corresponding to the above-mentioned silicone compounds, except that the silicon atoms are bonded directly to one another instead of via oxygen atoms. Examples of silanes having a chain backbone structure include those of the formula:

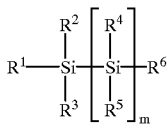

where $R^1$ and $R^6$ are independently hydrogen, methyl, or phenyl; $R^2$, $R^3$, $R^4$, and $R^5$ are independently methyl or phenyl; and m is from 1 to 100, preferably from 1 to 25, and more preferably from 1 to 4. The silanes or disilanes include, as non-limiting examples, dimethylphenylsilane, phenytrimethylsilane, triethylsilane, and hexamethyldisilane. Useful alkoxysilanes are those with at least one silicon-hydrogen bond.

Preferred organosilicon selectivating agents useful for selectivation of molecular sieves include, for example, dimethylphenylmethyl polysiloxane (e.g., Dow-550) and phenylmethyl polysiloxane (e.g., Dow-710). Dow-550 and Dow-710 are available from Dow Chemical Co., Midland, Mich.

As noted elsewhere herein, the catalyst can optionally be preselectivated by exposure to one or more ex situ selectivation treatments with a silicon compound in a liquid carrier, each treatment being followed by calcination of the treated material in an oxygen-containing atmosphere, e.g., air. Thus, the molecular sieve, e.g., HZSM-5, is treated at least once, preferably at least twice, more preferably at least 3 times, e.g., from 4 to 6 times, with a fluid medium comprising an organosilicon compound and a carrier fluid. The organosilicon compound may be present in the form of a solute dissolved in the liquid carrier or in the form of emulsified droplets in the liquid carrier.

The carrier fluid may be water, an organic fluid, or a combination thereof Various organic compounds and combinations thereof have been employed as carrier fluids for the silicon selectivating agent. For example, U.S. Pat. Nos. 4,145,3 15; 4,127,616; 4,090,981; and 4,060,568 describe the use of inter alia $C_{5-7}$ alkanes as solvents for silicon impregnation. Such organic carriers may linear, branched, or cyclic hydrocarbons having five or more, especially 7 or more, carbon atoms per molecule, e.g., alkanes, such as heptane, octane, nonane, decane, undecane, and dodecane. Mixtures of low volatility organic compounds, such as hydrocracker recycle oil, may be employed as carriers. Particularly preferred organic carriers are decane and dodecane.

When water is used as the carrier medium, the organosilicon compound may be distributed therein in solution or in emulsion form. Particularly when the liquid medium comprises an emulsion of the silicon compound in water, the carrier medium may also comprise an emulsifying agent, such as a surfactant. When the organosilicon preselectivating agent is present in the form of a water soluble compound in an aqueous solution, the organosilicon compound may be substituted with or more hydrophilic functional groups or moieties, which serve to promote the overall water solubility of the organosilicon compound. These hydrophilic functional groups may include one or more organoamine groups, such as —$N(CH_3)_3$, —$N(C_2H_4)_3$, and —$N(C_3H_7)_3$. A preferred water-soluble organosilicon preselectivating agent is an n-propylamine silane, available as Hydrosil 2627 from H üls America. Particular water-soluble organosilicon compounds, which may be used for multiple impregnations of the present catalyst, are referred to as aminosilane polymers in U.S. Pat. No. 5,371,312.

When the molecular sieve is preselectivated by a single or multiple impregnation technique, the molecular sieve is calcined after each impregnation to remove the carrier and to convert the liquid organosilicon compound to a solid residue material thereof This solid residue material is referred to herein as a siliceous solid material, insofar as this material is believed to be a polymeric species having a high content of silicon atoms in its structure. However, this siliceous solid residue material may also comprise residual carbon atoms in its structure, resulting from the organic portion of the organosilicon compound.

Following each impregnation, the molecular sieve may be calcined, by heating at a rate of from 0.2° C./min to 5° C./min, to a temperature greater than 200° C., but below the temperature at which the crystallinity of the molecular sieve is adversely affected. This calcination temperature is typically below about 600° C., generally being within the approximate range of 350° C. to 550° C. The duration of calcination at the calcination temperature may be from 1 hr to 24 hr, e.g., from 2 hr to 6 hr.

The impregnated molecular sieve may be calcined in an inert or oxidizing atmosphere. An example of such an inert atmosphere is a nitrogen ($N_2$) atmosphere. An example of an oxidizing atmosphere is an oxygen-containing atmosphere, such as air. Calcination may take place initially in an inert, e.g., $N_2$ atmosphere, followed by calcination in an oxygen-containing atmosphere, such as air or a mixture of air and $N_2$. Calcination should be performed in an atmosphere substantially free of water vapor to avoid undesirable uncontrolled steaming of the molecular sieve. The molecular sieve may be calcined once or more than once following each impregnation. The various calcinations following each impregnation need not be identical, but may vary with respect to the calcination temperature, the rate of temperature rise, the atmosphere, and the duration of calcination.

The amount of siliceous residue material that is deposited on the molecular sieve or bound molecular sieve is dependent upon a number of factors including the temperatures of the impregnation and calcination steps, the concentration of the organosilicon compound in the carrying medium, the degree to which the catalyst has been dried prior to contact with the organosilicon compound, the atmosphere used in the calcination, and duration of the calcination. A suitable amount of silicon on the catalyst is greater than about 5 wt %, exclusive of the silica present in the binder or in the molecular sieve itself.

The catalyst may be subjected to steaming conditions sufficient to increase or decrease the activity and/or selectivity of the catalyst as desired. Such conditions are disclosed, for example, in U.S. Pat. No. 5,349,114. The steaming conditions may include a temperature of from about 100° C. to about 800° C., e.g., from about 175° C. to about 325° C., with from about 1% to about 100% steam, e.g., from about 50% to about 100% steam, at a pressure of from about 0.01 psia (69 Paa) to about 5000 psia (34474 kpaa), and for a duration of from about 0.1 hr to about 24 hr, e.g., from about 3 hr to about 6 hr. Excessive steaming or steaming under severe conditions may be detrimental to the activity and selectivity of the catalyst.

The present catalyst may comprise at least 0.03 wt %, e.g., at least 0.1 wt %, of alkali metal or alkaline earth metal, e.g., an amount effective to achieve the desired activity/ selectivity. Particular alkali metals include Ii, Na, K, Rb, and Cs. Particular alkaline earth metals include Mg, Ca, Sr, and Ba. The alkali metal or alkaline earth metal may be added by contacting the catalyst, in particular, the molecular sieve component of the catalyst, either before or after selectivation, with an aqueous solution containing an alkali metal, ion of an alkali metal, alkaline earth metal, or ion of an alkaline earth metal, optionally washing off excess solution using water or another solvent, and then drying the treated catalyst. The present alkali metal or alkaline earth metal incorporation or ion exchange procedure may be used to decrease the activity of the catalyst. The activity may be adjusted on a small scale to fine-tune batches of the catalyst for a particular use or the activity may be adjusted on a major scale to convert the catalyst from one type to another, thereby providing a means to manufacture different catalysts for different uses. The amount of alkali metal or alkaline earth metal ions incorporated into the catalyst will generally negatively affect catalyst activity, and can be selected as desired to fine-tune the activity of the catalyst. Thus, smaller amounts of alkali metal or alkaline earth metal will reduce the alpha value of the catalyst by a smaller amount, e.g., about 10%, and larger amounts of alkali metal or alkaline earth metal will reduce the alpha value of the catalyst by a larger amount, e.g., by 50% or more.

The present catalyst may be subjected to controlled coking. This controlled coking procedure is also referred to herein as coke selectivation. This optional coke selectivation may involve contacting the catalyst with a thermally decomposable organic compound at an elevated temperature in excess of the decomposition temperature of the compound but below the temperature at which the crystallinity of the molecular sieve is adversely affected. This contact temperature may be, for example, less than 650° C. The catalyst may be coked in a reactor or other vessel that is different than that used for the ethylbenzene conversion, followed by transport of the coked catalyst to the ethylbenzene conversion reactor. Performance of coke selectivated catalyst for ethylbenzene conversion is not significantly degraded by the handling associated with transporting the catalyst between the reactor used to coke selectivated the catalyst and the ethylbenzene conversion catalyst. Coke selectivation is described in U.S. Pat. Nos. 5,234,875; 4,581,215; 4,508,836; 4,358,395; 4,117,026; and 4,097,543.

Organic materials useful for this coke selectivation process encompass a wide variety of compounds, including by way of example, hydrocarbons, such as paraffins, cycloparaffins, olefins, cycloolefins and aromatics; oxygen-containing organic compounds, such as alcohols, aldehydes, ethers, ketones and phenols; and heterocyclics, such as furans, thiophenes, pyrroles and pyridines. A hydrogen co-feed may be used to deter the excessive build-up of coke. Further details regarding coke selectivation techniques are provided in the U.S. Pat. No. 4,117,026, as well as in PCT Publication No. WO94/27934. An organosilicon cofeed may be, optionally, included along with the organic material feed used for coke selectivation. this organosilicon material may be selected from the organosilicon compounds mentioned hereinabove for use in the in situ selectivation of the catalyst.

While not wishing to be bound by any theory, it is possible that the selectivity of the present ethylbenzene conversion catalyst is obtained by producing changes in the diffusion properties of the molecular sieve that favor the desired reactions and inhibit undesired reactions.

EXAMPLE 1

An HZSM-5A catalyst preparation (65/35 zeolite/binder) was prepared according to a multiple silicone coating preselectivation procedure. In brief, the catalyst was contacted with Dow-550 dissolved in decane. After the decane was stripped, the catalyst was calcined at temperatures up to 1000° F. in nitrogen, and then in air. This procedure was repeated three more times to yield a four-times treated catalyst.

EXAMPLE 2

Platinum was exchanged into a catalyst prepared as described in Example 1, using a conventional exchange technique to produce a modified catalyst containing about 0.1 wt % Pt. Specifically, 0.0271 g of $Pt(NH_3)_4Cl_2 \cdot H_2O$ was dissolved in about 60 ml distilled, deionized water in a beaker with a stirbar. The beaker was equipped to support a Büchner funnel (a "ceramic thimble"). Catalyst (15 g) was loaded into a Büchner funnel, which was then placed in this solution. The pH of the solution then dropped fairly rapidly to about pH 3. Ammonium hydroxide (0.1 N) was added dropwise to maintain the pH at between about pH 7 and about pH 4. Following the exchange, the catalyst was dried and calcined at 350° C. for 2 hr. The calcined catalyst was then crushed and sized to 14/20 mesh.

EXAMPLE 3

A microunit evaluation was conducted in an automated unit with on-line gas chromatograph (GC) sampling. Catalyst (0.75 g) was loaded into a ⅜-inch diameter, stainless steel tube reactor (with sand as inert packing material). The reactor was pressurized to 150 psig with $N_2$, and heated to 350° C. under flowing nitrogen. The catalyst was then reduced by interrupting the $N_2$ flow, and introducing $H_2$ flow at a rate of 100 mL/min. After reducing for 2 hr, the reactor was heated to reaction temperature and feed was introduced. The feed was blended from meta-xylene, orho-xylene, and ethylbenzene (Aldrich "HPLC Grade").

Catalytic evaluation was conducted at 10 $hr^{-1}$ WHSV, 1 $H_2$/HC, and about 150 psig pressure. The results are presented in Table 1, below.

TABLE 1

| Yields (wt %) | Feed | Results |
|---|---|---|
| $C_5^-$ | — | 5.3 |
| Benzene | — | 14.3 |
| Toluene | — | 1.6 |
| Ethylbenzene | 20 | 0.15 |
| Para-Xylene | 0 | 0.7 |
| Meta-Xylene | 60 | 58.2 |
| Ortho-Xylene | 20 | 19.7 |
| $C_9^+$ | — | 0.1 |
| Ethylbenzene Conversion (%) | — | 99.3 |
| Xylene Loss | — | 1.7 |

The results of this evaluation, as summarized above, demonstrate that extremely high ethylbenzene conversion can be achieved using the method of the invention. Although para-xylene was not present as a feed component, the amount of para-xylene formed was very small. Para-xylene can also be selectively converted to toluene and trimethylbenzene (via disproportionation) or to toluene with benzene (via reverse toluene disproportionation). Given these results, we calculated meta-xylene purity, defined as the amount of meta-xylene divided by the sum of the amounts of meta-xylene and its coboilers (i.e., ethylbenzene, para-xylene). In this case the met-xylene purity was 98.6%.

These results clearly show that high-purity meta-xylene can be produced by catalytically converting ethylbenzene, coupled with distillation. Although this feed did not include para-xylene, its inclusion in the feed would not be expected to significantly change these results. Furthermore, benzene may be cofed to facilitate the conversion of para-xylene to compounds such as toluene and trimethylbenzene.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

What is claimed is:

1. A process for producing purified meta-xylene comprising:
   converting a hydrocarbon feedstream comprising at least 5 wt. % ethylbenzene, at least 20 wt. % meta-xylene, and less than 5 wt. % para-xylene over a catalyst comprising a single molecular sieve under ethylbenzene conversion conditions sufficient to provide a primary product stream depleted of more than 90% of the ethylbenzene in the feedstream; and
   stripping benzene and/or toluene by-products from the primary product stream to provide a secondary product stream comprising at least 75 wt. % mixed ortho-xylene and meta-xylene; and
   splitting the secondary product stream by removing ortho-xylene and heavier materials present therein to provide a tertiary product stream comprising at least about 85 wt. % meta-xylene.

2. A process according to claim 1, further comprising;
   distilling the tertiary product stream to obtain a distillate having further increased meta-xylene content.

3. A process according to claim 2, wherein the distillate comprises at least 98 wt % meta-xylene.

4. A process according to claim 1, further comprising separating para-xylene from a mixed $C_8$ hydrocarbon feedstream comprising para-xylene, ortho-xylene, meta-xylene, and ethylbenzene, to provide the meta-xylene-rich feedstream.

5. A process according to claim 1, further comprising cofeeding benzene with the hydrocarbon feedstream.

6. A process according to claim 1, wherein the hydrocarbon feedstream comprises from about 5 wt % to about 20 wt % ethylbenzene, from about 20 wt % to about 80 wt % meta-xylene, from about 5 wt % to about 30 wt % ortho-xylene, and from about 0.5 wt % to about 5 wt % para-xylene.

7. A process according to claim 1, wherein the hydrocarbon feedstream comprises from about 5 wt % to about 20 wt % ethylbenzene, from about 50 wt % to about 65 wt % meta-xylene, from about 20 wt % to about 30 wt % ortho-xylene, and from about 0.5 wt % to about 5 wt % para-xylene.

8. A process according to claim 1, wherein the ethylbenzene conversion conditions comprise a temperature of from about 200° C. to about 550° C., a pressure of from 0 psig to about 1,000 psig, a WHSV of between about 0.1 $hr^{-1}$ and about 200 $hr^{-1}$, and a $H_2$/HC molar ratio of between about 0.2 and about 10.

9. A process according to claim 1, wherein the ethylbenzene conversion conditions comprise a temperature of from about 325° C. to about 475° C., a pressure of from about 50 psig to about 400 psig, a WHSV of between about 3 $hr^{-1}$ and about 50 $hr^{-1}$, and a $H_2$/HC molar ratio of between about 1 and about 5.

10. A process according to claim 1, wherein the molecular sieve is selected from the group consisting of ZSM-5, ZSM-11, ZSM-12, ZSM-21, ZSM-22, ZSM-23, ZSM-35, ZSM-38, ZSM-48, ZSM-57, ZSM-58, SAPO-5, SAPO-11, zeolite Beta, zeolite X, zeolite Y, MCM-22, MCM-36, MCM49, and MCM-56.

11. A process according to claim 10, wherein the molecular sieve is ZSM-5.

12. A process according to claim 1, wherein the catalyst has been modified by ex situ selectivation, in situ selectivation, coke selectivation, steaming, or a combination thereof.

13. A process according to claim 1, wherein the catalyst has been modified to include a hydrogenation-dehydrogenation functional metal selected from the group consisting of metals from Groups 3 to 15 of the periodic table.

14. A process according to claim 13, wherein the catalyst has been modified to include platinum as the hydrogenation-dehydrogenation functional metal.

15. A process according to claim 13, wherein the catalyst has been modified to include rhenium as the hydrogenation-dehydrogenation functional metal.

16. A process according to claim 1, wherein the catalyst has an ortho-xylene $t_{0.3}$ sorption time of greater than about 50 min at 4.5±0.8 mm Hg and 120° C.

17. A process according to claim 1, wherein the catalyst produces less than 12 wt % para-xylene when contacting a feed containing 60 wt % meta-xylene, 20 wt % ortho-xylene, and 20 wt % ethylbenzene at a temperature of 426.7° C, a pressure of 150 psig, a WHSV of 20 $hr^{-1}$, and a $H_2$/HC molar ratio of 1.

18. A process for production of purified meta-xylene from a mixed $C_8$ aromatic feedstream, comprising:
   separating para-xylene from a mixed $C_8$ hydrocarbon fluid comprising para-xylene, ortho-xylene, meta-xylene, and ethylbenzene, to provide a hydrocarbon feedstream comprising at least 5 wt % ethylbenzene, at least 20 wt % meta-xylene, and less than 5 wt % para-xylene;
   converting the hydrocarbon feedstream over a catalyst comprising a single molecular sieve under ethylbenzene conversion conditions sufficient to provide a primary product stream depleted of more than 50% of the ethylbenzene present in the feedstream;
   stripping benzene and/or toluene by-products from the primary product stream to provide a secondary product stream comprising at least 75 wt % mixed ortho-xylene and meta-xylene; and
   splitting the secondary product stream by removing orthoxylene and heavier materials present therein to provide a tertiary product stream comprising at least 95 wt % meta-xylene.

* * * * *